United States Patent
Yu et al.

(10) Patent No.: US 10,229,488 B2
(45) Date of Patent: Mar. 12, 2019

(54) METHOD AND SYSTEM FOR DETERMINING A STAGE OF FIBROSIS IN A LIVER

(75) Inventors: Hanry Yu, Singapore (SG); Dean Tai, Singapore (SG); Yuting He, Singapore (SG); Shuoyu Xu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 430 days.

(21) Appl. No.: 13/638,930

(22) PCT Filed: Mar. 31, 2011

(86) PCT No.: PCT/SG2011/000133
§ 371 (c)(1),
(2), (4) Date: Oct. 1, 2012

(87) PCT Pub. No.: WO2011/123068
PCT Pub. Date: Oct. 6, 2011

(65) Prior Publication Data
US 2013/0030305 A1 Jan. 31, 2013

Related U.S. Application Data

(60) Provisional application No. 61/319,673, filed on Mar. 31, 2010.

(51) Int. Cl.
*G06T 7/00* (2017.01)
*A61B 5/00* (2006.01)

(52) U.S. Cl.
CPC .......... *G06T 7/0012* (2013.01); *A61B 5/0084* (2013.01); *A61B 5/4244* (2013.01);
(Continued)

(58) Field of Classification Search
CPC ... A61B 5/0084; A61B 5/4244; A61B 5/7267; A61K 31/551; A61K 9/0019
See application file for complete search history.

(56) References Cited

U.S. PATENT DOCUMENTS 7,280,604 B2 10/2007 Giannakis et al.
7,394,933 B2 7/2008 Tek et al.
(Continued)

FOREIGN PATENT DOCUMENTS

JP 2006-073669 A 3/2006
WO WO 2006/079143 A1 8/2006
(Continued)

OTHER PUBLICATIONS

Weyn, Barbara, et al. "Computer-assisted differential diagnosis of malignant mesothelioma based on syntactic structure analysis." Cytometry 35.1 (1999): 23-29.*
(Continued)

*Primary Examiner* — Carolyn Pehlke
(74) *Attorney, Agent, or Firm* — Womble Bond Dickinson (US) LLP

(57) ABSTRACT

A method for determining a stage of fibrosis in a liver is disclosed. The method comprises the steps of: (1a) obtaining input data relating to the liver, the input data being generated using a second harmonic generation based imaging system; (1b) identifying a plurality of morphological features of the liver from the input data relating to the liver; (1c) generating a plurality of measurements based on the identified plurality of morphological features; and (1d) determining the stage of fibrosis in the liver based, on the generated plurality of measurements.

22 Claims, 6 Drawing Sheets

(52) U.S. Cl.
CPC ... *A61B 5/7267* (2013.01); *G06T 2207/10064* (2013.01); *G06T 2207/10068* (2013.01); *G06T 2207/20036* (2013.01); *G06T 2207/30056* (2013.01)

(56) References Cited

U.S. PATENT DOCUMENTS

| | | | |
|---|---|---|---|
| 7,693,041 | B2 | 4/2010 | Joo et al. |
| 8,004,959 | B2 | 8/2011 | Dent |
| 8,514,788 | B2 | 8/2013 | Fujita et al. |
| 8,576,823 | B2 | 11/2013 | Pajukoski et al. |
| 2004/0082303 | A1 | 4/2004 | Giannakis et al. |
| 2006/0215349 | A1 | 9/2006 | Yao et al. |
| 2008/0015448 | A1 | 1/2008 | Keely et al. |
| 2008/0095039 | A1 | 4/2008 | Joo et al. |
| 2008/0123593 | A1 | 5/2008 | Fujita et al. |
| 2008/0285534 | A1 | 11/2008 | Dent |
| 2009/0185980 | A1 | 7/2009 | Dong et al. |
| 2009/0323059 | A1 | 12/2009 | Sun et al. |

FOREIGN PATENT DOCUMENTS

| | | | |
|---|---|---|---|
| WO | WO 2008/002278 A1 | | 1/2008 |
| WO | WO 2008002278 A1 | * | 1/2008 |
| WO | WO 2008/136768 A1 | | 11/2008 |

OTHER PUBLICATIONS

Cox, Guy, et al. "3-dimensional imaging of collagen using second harmonic generation." Journal of structural biology 141.1 (2003): 53-62.*

Region Growing (https://www.cse.unr.edu/~bebis/CS791E/Notes/RegionGrowing.pdf, Dec. 27, 2005).*

R. Bowen (Hepatic Histology: The Lobule, http://arbl.cymbs.colostate.edu/hbooks/pathphys/digestion/liver/histo_lobule.html, Oct. 26, 2003).*

PCT International Search Report for PCT Counterpart Application No. PCT/SG2011/000133 containing Communication relating to the Results of the International Search Report, 4 pages, (dated Jun. 6, 2011).

PCT Written Opinion of the International Searching Authority for PCT Counterpart Application No. PCT/SG2011/000133, 7 pages, (dated Jun. 6, 2011).

PCT Notification concerning Transmittal of International Preliminary Report on Patentability (Chapter I of the Patent Cooperation Treaty) for PCT Counterpart Application No. PCT/SG2011/000133, 9 pages, (dated Oct. 11, 2012).

Wanxin Sun, et al., "Nonlinear Optical Microscopy: Use of Second Harmonic Generation and Two-Photon Microscopy for Automated Quantitative Liver Fibrosis Studies", Journal of Biomedical Optics, vol. 13, No. 6, pp. 064010-1-064010-7, (Nov./Dec. 2008).

Dean C. S. Tai, et al., "Fibro-C-Index: Comprehensive, Morphology-Based Quantification of Liver Fibrosis using Second Harmonic Generation and Two-Photon Microscopy", Journal of Biomedical Optics, vol. 14, No. 4, pp. 044013-1-044013-10, (Jul./Aug. 2009).

Paul J. Campagnola, et al., "High-Resolution Nonlinear Optical Imaging of Live Cells by Second Harmonic Generation", Biophysical Journal, vol. 77, pp. 3341-3349, (Dec. 1999).

PCT International Search Report for PCT Counterpart Application No. PCT/SG2011/0001271, 3 pgs. (dated Sep. 29, 2011).

PCT Written Opinion of the International Searching Authority for PCT Counterpart Application No. PCT/SG2011/000271, 4 pgs. (dated Sep. 29, 2011).

PCT Notification concerning Transmittal of International Preliminary Report on Patentability (Chapter I of the Patent Cooperation Treaty) for PCT Counterpart Application No. PCT/SG2011/000271, 6 pgs., (dated Feb. 14, 2013).

Xiang Deng, et al., "Editorial: 3D Segmentation in the Clinic: A Grand Challenge 11—Liver Tumor Segmentation", MICCAI 2008 Workshop "3D Segmentation in the Clinic: A Grand Challenge II", retrieved from http://www.grand-challenge2008.bigr.nl/proceedings/liver/articles.html, 4 pgs., (Sep. 2008).

Mario A. Di Pascuale, et al., "Corneal Deturgescence After Descemet Stripping Automated Endothelial Keratoplasty Evaluated by Visante Anterior Segment Optical Coherence Tomography", Americal Journal of Ophthalmology, vol. 148, No. 1, pp. 32-37.e1, (Jul. 2009).

Xiao Chen He, et al., "Corner Detector Based on Global and Local Curvature Properties", Optical Engineering, vol. 47, No. 5, pp. 057008-1-057008-12, (May 2008).

Marco Lombardo, et al., "Analysis of Posterior Donor Corneal Parameters 1 year after Descemet Stripping Automated Endothelial Keratoplasty (DSAEK) Triple Procedure", Graefe's Archive for Clinical and Experimental Ophthalmology, vol. 248, pp. 421-427, (2010).

Laurence S. Lim, et al., "Corneal Imaging With Anterior Segment Optical Coherence Tomography for Lamellar Keratoplasty Procedures", American Journal of Ophthalmology, vol. 145, No. 1, pp. 81-90, (Jan. 2008).

Victor Penner, et al., "Use of the Visante for Anterior Segment Ocular Coherence Tomography", Techniques in Ophthalmology, vol. 5, No. 2, pp. 67-77, (2007).

Leonard H. Yuen, et al., "Biometry of the Cornea and Anterior Chamber in Chinese Eyes: an Anterior Segment Optical Coherence Tomography Study." Investigative Ophthalmology & Visual Science 51.7 (2010): 3433-3440.

D.C.S. Tai, et al., "Automated Algorithm for Standardized Quantification on Liver Fibrosis using Second Harmonic Generation Microscopy", IEEE Photonics Global Conference (IPGC), 4 pp., (2008).

Luc Gailhouste, et al., "Fibrillar Collagen Scoring by Second Harmonic Microscopy: A New Tool in the Assessment of Liver Fibrosis", Journal of Hepatology, vol. 52, pp. 398-406, (2010).

Pierre Bedossa, "Harmony in Liver Fibrosis . . . ", Journal of Hepatology, vol. 52, pp. 313-314, (2010).

PCT International Search Report for PCT Counterpart Application No. PCT/SG2011/000080 containing Communication relating to the Results of the International Search Report, 2 pgs. (dated Apr. 18, 2011).

PCT Written Opinion of the International Searching Authority for PCT Counterpart Application No. PCT/SG2011/000080, 5 pgs. (dated Apr. 18, 2011).

Xinyu Zhang, et al., "Network Coding Aware Dynamic Subcarrier Assignment in OFDMA Wireless Networks", IEEE International Conference on Communications (ICC 2008), pp. 2735-2739, (2008).

Yuedong Xu, et al., "Analysis and Scheduling of Practical Network Coding in OFDMA Relay Networks", Computer Networks, vol. 53, pp. 2120-2139, (2009).

PCT International Search Report for PCT Counterpart Application No. PCT/SG2011/000141 containing Communication relating to the Results of the International Search Report, 5 pgs. (dated Jun. 7, 2011).

PCT Written Opinion of the International Searching Authority for PCT Counterpart Application No. PCT/SG2011/000141, 7 pgs. (dated Jun. 7, 2011).

PCT International Preliminary Report on Patentability (Chapter II of the Patent Cooperation Treaty) for PCT Counterpart Application No. PCT/SG2011/000141, 15 pgs., (dated Jun. 20, 2012).

Meng Qin, et al., "Photovoltaic Characteristics in Polycrystalline and Epitaxial $(Pb_{0.97}La_{0.03})(Zr_{0.52}Ti_{0.48})O_3$ Ferroelectric Thin Films Sandwiched between Different Top and Bottom Electrodes", Journal of Applied Physics, vol. 105, pp. 061624-1-061624-7, (2009).

Meng Qin, et al., "Stability and Magnitude of Photovoltage in Ferroelectric $(Pb_{0.97}La_{0.03})(Zr_{0.52}Ti_{0.48})O_3$ Thin Films in Multi-Cycle UV Light Illumination", Integrated Ferroelectrics, vol. 95, pp. 105-116, (2007).

Frank McNally, et al., "Fatigue Properties of Lanthanum Strontium Manganate-Lead Zirconate Titanate Epitaxial Thin Film Heterostructures Produced by a Chemical Solution Deposition Method", Journal of Materials Research, vol. 15, No. 7, pp. 1546-1550, (Jul. 2000).

Meng Qin, et al., "Development of Low-cost Ferroelectric PLZT Devices for Photovoltaic Power Generation", IEEE ICSET 2010 in Kandy, Sri Lanka, 5 pp., (Dec. 6-9, 2010).

(56) References Cited

OTHER PUBLICATIONS

I. Boerasu, et al., "Competition between Ferroelectric and Semiconductor Properties in Pb($Zr_{0.65}Ti_{0.35}$)$O_3$ Thin Films Deposited by Sol-Gel", Journal of Applied Physics, vol. 93, No. 8, pp. 4776-4783, (Apr. 15, 2003).
D. Goodman, Z., Grading and staging systems for inflammation and fibrosis in chronic liver diseases. Journal of Hepatology, 2007. 47: p. 598-607.
Standish, R.A., et al. An appraisal of the histopathological assessment of liver fibrosis. Gut, 2006. 55: p. 569-578.
Knodell, R., et al., Formulation and application of a numerical scoring system for assessing histological activity in asymptomatic chronic active hepatitis. Hepatology, 1981. 1(5): p. 431-5.
Scheuer, P., Classification of chronic viral hepatitis: a need for reassessment. Journal of Hepatology, 1991.13: p. 372-4.
Ishak, K., et al., Histological grading and staging of chronic hepatitis. Journal of Hepatology, 1995. 22(6): p. 696-9.
Bedossa, P. and T. Poynard, The METAVIR cooperative study group. An algorithm for the grading of activity in chronic hepatitis C. Journal of Hepatology, 1996. 24(289-93).
Bedossa, P., et al., Intraobserver and interobserver variations in liver biopsy interpretation in patients with chronic hepatitis C. The French METAVIR Cooperative Study Group. Hepatology, 1994. 20(1): p. 15-20.
Gronbaek, K., et al., Interobserver variation in interpretation of serial liver biopsies from patients with chronic hepatitis C. Journal of Viral Hepatitis, 2002. 9(6): p. 443-449.
Westin, J., et al., Interobserver study of liver histopathology using the Ishak score in patients with chronic hepatitis C virus infection. Liver, 1999. 19(3): p. 183-187.
Masseroli, M. et al., Automatic quantification of liver fibrosis: design and validation of a new image analysis method: comparison with semi-quantitative indexes of fibrosis. Journal of Hepatology, 2000. 32(3): p. 453-64.
O'Brien, M., et al., An assessment of digital image analysis to measure fibrosis in liver biopsy specimens of patients with chronic hepatitis C. American Journal of Clinical Pathology, 2000. 114(5): p. 712-8.
Wright, M., et al., Quantitative versus morphological assessment of liver fibrosis: semi-quantitative scores are more robust than digital image fibrosis area estimation. Liver International, 2003. 23(1): p. 28-34.
Lazzarini, A.L., et al., Advances in digital quantification techniques enhance discrimination between mild and advanced liver fibrosis in chronic hepatitis C. Liver International, 2005. 25: p. 1142-1149.
Friedenberg, M.A., et al., Simplified method of hepatic fibrosis quantification: design of a new morphometric analysis application. Liver International, 2005. 25: p. 1156-1161.
Matalka, I.I., O. M.Ai-Jarrah, and T.M. Manasrah, Quantitative assessment of liver fibrosis: a novel automated image analysis method. Liver International, 2006(26): p. 1054-1064.
Goodman, Z.D., et al., Progression of Fibrosis in Advanced Chronic Hepatitis C: Evaluation by Morphometric Image Analysis. Hepatology, 2007. 45(4): p. 886-94.
Dioguardi, N., et al., Metrically measuring liver biopsy: A chronic hepatitis B and C computer-aided morphologic description. World Journal of Gastroenterology, 2008. 14(48): p. 7335-7344.
Otsu, N., A Threshold Selection Method from Gray-Level Histograms. Systems, Man and Cybernetics, IEEE Transactions on, 1979. 9(1): p. 62-66.
P. Lloyd, S., Least Squares Quantization in PCM. IEEE Transactions on Information Theory, 1982. 28(2): p. 129-137.
Shapiro, L.G. and G.C. Stockman, Computer Vision. 2001: Upper Saddle River, NJ: Prentice Hall.
Bezdek, J.C., Pattern Recognition with Fuzzy Objective Function Algorithms. 1981.
Dempster, A.P., N.M. Laird, and D.B. Rubin, Maximum Likelihood from Incomplete Data via theEM algorithm. Journal of the Royal Statistical Society, 1977. Series B, 39(1): p. 1-38.
D.M. Green and J.M. Swets (1966). Signal detection theory and psychophysics. New York: John Wiley and Sons Inc.
Luc Vincent: Morphological grayscale reconstruction in image analysis: applications and efficient algorithms. IEEE Trans. on Image Processing, vol. 2, No. 2, pp. 176-201, Apr. 1993.
R. Gonzalez and R. Woods, Digital Image Processing, Addison-Wesley Publishing Company, 1992, pp. 518, 512, 550.
Barber, C.B., Dobkin, D.P., and Huhdanpaa, H.T., "The Quickhull algorithm for convex hulls," ACM Trans. on Mathematical Software, 22(4):469-483, Dec. 1996, http://www.qhull.org.

\* cited by examiner

METHOD AND SYSTEM FOR DETERMINING A STAGE OF FIBROSIS IN A LIVER

CROSS-REFERENCE TO RELATED APPLICATIONS

This patent application is a U.S. National Phase application under 35 U.S.C. § 371 of International Application No. PCT/SG2011/000133, filed Mar. 31, 2011, entitled A METHOD AND SYSTEM FOR DETERMINING A STAGE OF FIBROSIS IN A LIVER, which claims priority to U.S. provisional patent application No. 61/319,673. filed Mar. 31, 2010.

FIELD OF THE INVENTION

The present invention relates to a method and system for determining a stage of fibrosis in a liver. The present invention utilizes a method for generating a plurality of measurements relating to a plurality of morphological features in the liver.

BACKGROUND OF THE INVENTION

The stage of a disease is a measure of how far the disease has progressed in its natural history, with the end stage usually resulting in the death of a patient with the disease and/or the failure of an organ with the disease. In other words, the grade (or stage) of a disease reflects how quickly the disease is progressing to the end stage [1].

In most forms of chronic liver diseases, the end stage involves a large amount of fibrosis or cirrhosis, whereas lower amounts of fibrosis or cirrhosis are present in the liver during the earlier stages. Descriptive or semi-quantitative scoring systems may be used to grade and stage liver biopsy samples. For example, a traditional method of assessing the degree of fibrosis in a liver biopsy sample may involve giving the liver biopsy sample a grade ("absent", "mild", "moderate", or "severe") based on the amount of fibrosis in the liver biopsy sample. Furthermore, in a first semi-quantitative scoring system implemented in the 1980s, a range of numbers representing different categories was allocated to different pathological features on the basis of their severity [2]. Examples of routinely used scoring systems also include the Knodell histological activity index (HAI) [3], Scheuer [4], Ishak [5] and METAVIR[6] systems. However, pathological features used in these systems are usually not clearly defined and are somewhat ambiguous. As a result, the grading and staging scores obtained in these systems tend to rely on the observers' subjective opinions. Therefore, using these systems, inter- and intra-observer variations can be as high as 35%, making it difficult to obtain highly reproducible results [7-9].

In several studies as shown in Table 1 [10-17], liver fibrosis is quantified using image analysis. The computer-aided systems in these studies aim to provide objective quantitative measurements which can help reduce observer discrepancies. However, all of the systems in the studies shown in Table 1 require stained biopsy samples and thus, are faced with the problem of staining variations. Also, in most of these systems, the only measurement to grade and stage fibrosis is the fibrosis area. However, other pathological features (such as fibrosis architecture) often play an equally important, if not more important, role in grading and staging fibrosis [2]. Furthermore, although some correlations between the fibrosis area and the semi-quantitative scores were reported in the studies, the amount of fibrosis is not specifically addressed in any of the scoring systems.

TABLE 1

| Authors | Year | Sample Preparation Technique | Parameter(s) Measured | Quantification Algorithm(s) Used |
|---|---|---|---|---|
| M. O'Brien et al. [11] | 2000 | Mallory trichrome stained | Fibrosis area | Manual thresholding |
| M. Masseroli et al. [10] | 2000 | Sirius Red stained | Perisinusoidal, Portal-peri-portal, Septal fibrosis area | Kurita's thresholding |
| Wright M et al. [12] | 2003 | Picrosirius Red stained | Fibrosis area | Thresholding using histograms |
| A. Lazzarini et al. [13] | 2005 | Trichrome stained | Fibrosis area | Manual thresholding |
| M Friedenberg et al. [14] | 2005 | Masson's trichrome stained | Fibrosis area | Manual thresholding |
| I Matalka et al. [15] | 2006 | Van Geison-stained | 54 image features | Two-level Neural Network |
| Z. D Goodman et al. [16] | 2007 | Sirius Red stained | Fibrosis area, Fibrosis volume | Optical polarization imaging |
| N. Dioguardi et al. [17] | 2008 | Sirius Red stained | Survival parenchyma surface, Inflammatory basin, Coefficient of inflammatory activity, Fractal dimension of the fibrosis, Wrinkedness of fibrosis, Tectonic index | Fractal geometry, Hurst's exponent, Clustering |

SUMMARY OF THE INVENTION

The present invention aims to provide a new and useful method and system for determining a stage of fibrosis in a liver.

In general terms, the present invention proposes using multiple measurements generated based on a plurality of morphological features of a liver to determine the stage of fibrosis of the liver.

Specifically, a first aspect of the invention is a method for determining a stage of fibrosis in a liver, the method comprising the steps of: (1a) obtaining input data relating to the liver, the input data being generated using a second harmonic generation based imaging system; (1b) identifying a plurality of morphological features of the liver from the input data relating to the liver; (1c) generating a plurality of measurements based on the identified plurality of morphological features; and (1d) determining the stage of fibrosis in the liver based on the generated plurality of measurements.

The invention may alternatively be expressed as a computer system for performing such a method. This computer system may be integrated with a device for capturing images of a patient's liver such as a Second, Harmonic Generation based imaging system. The invention may also be expressed as a computer program product, such as one recorded on a tangible computer medium, containing program instructions operable by a computer system to perform the steps of the method.

BRIEF DESCRIPTION OF THE FIGURES

An embodiment of the invention will now be illustrated for the sake of example only with reference to the following drawings, in which:

FIG. 2(a) illustrates an image in a Second Harmonic Generation channel ("SHG image") comprised in input data to the method of FIG. 1 whereas FIGS. 2(b)-(f) illustrate segmented collagen areas in the SHG image of FIG. 2(a) obtained using different segmentation methods and a two-channel method used in a stage of the method of FIG. 1;

DETAILED DESCRIPTION OF THE EMBODIMENTS

Figure 1:
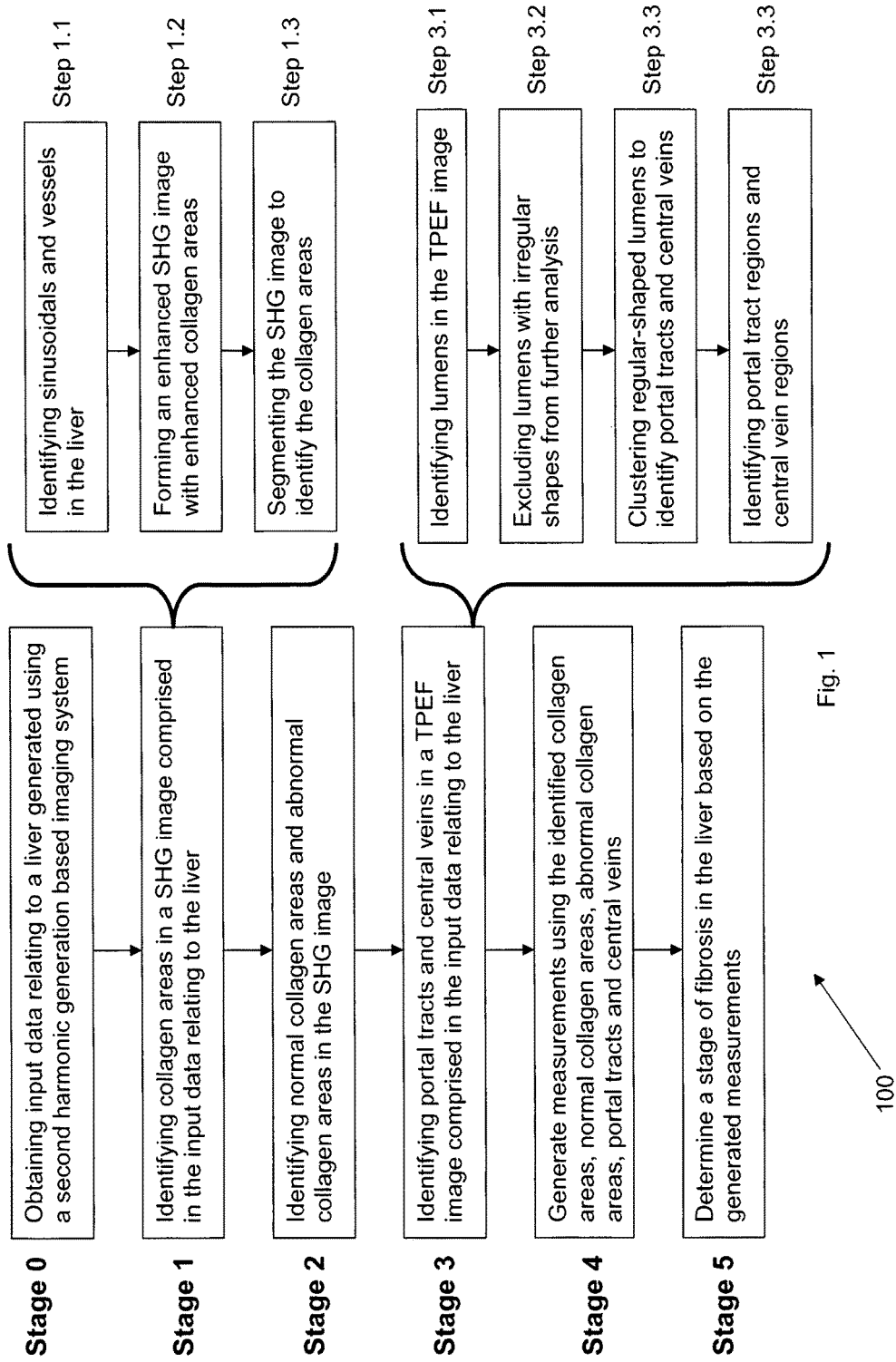
FIG. 1 illustrates a method for determining a stage of fibrosis in a liver according to an embodiment of the present invention.

Referring to FIG. 1, the steps are illustrated of a method 100 which is an embodiment of the present invention, and which determines a stage of fibrosis in the liver.

Method 100 comprises 6 stages. In Stage 0, input data relating to a liver (comprising liver tissue) is obtained. The input data is generated using a second harmonic generation based imaging system. For example, the input data may be acquired using an endoscope (in other words, using reflective mode imaging). The input data may also be acquired without staining the liver tissue. Furthermore, the input data comprises two images: a first image in the Two-Photon Excitation Fluorescence (TPEF) channel (i.e. "TPEF image") and a second image in the Second Harmonic Generation (SHG) channel (i.e. "SHG image"). The TPEF and SHG images respectively comprise information relating to the tissue structure in the liver and information relating to the collagen content in the liver. Furthermore, each of these images comprises a plurality of pixels. Note that Stage 0 may be omitted from method 100 and Stages 1-5 may be directly applied on a pre-generated image.

In Stage 1, areas of the liver comprising collagen (i.e. collagen areas) are identified in the SHG image. In Stage 2, areas of the liver comprising normal and abnormal collagen (i.e. normal collagen areas and abnormal collagen areas) are identified in the SHG image. In Stage 3, portal tracts and central veins are identified in the TPEF image and in Stage 4, a plurality of measurements are generated based on the identified collagen areas, normal collagen areas, abnormal collagen areas, portal tracts and central veins. In Stage 5, a stage of fibrosis in the liver is determined based on the generated measurements.

Stages 1-5 of method 100 will now be described in more detail. In the following description, the input data comprises two-dimensional (2D) data, in other words, the SHG and TPEF images are 2D images. However, note that the input data may also comprise three-dimensional (3D) data, in other words, the SHG and TPEF images may also be 3D images whereby each 3D image may comprise a stack of 2D images. In this case, stages 1-5 of method 100 may be performed on each 2D image in the stack independently whereby the stack may belong to either a 3D SHG image or a 3D TPEF image (whichever is applicable). The processed 2D images from each stage may then be registered to form a 3D image. The stage of fibrosis in the liver may be determined using measurements generated based on the morphological features identified from one or more of the 2D images in the stack.

Stage 1: Identifying Collagen Areas in the SHG Image

In Stage 1 of method 100, collagen areas in the SHG mage are segmented and identified. Stage 1 further comprises steps 1.1, 1.2 and 1.3 which will be described in more detail below.

In step 1.1, sinusoidals and vessels in the liver are identified by segmenting pixels in the TPEF image into different groups of pixels based on the intensities of the pixels. In one example, the pixels in the TPEF image are segmented or clustered into 3 different groups: (i) a first group comprising completely dark pixels which represent areas of vessels and spaces outside the liver tissue, (ii) a second group comprising dim pixels which represent sinusoidals and bile duct cannaliculi (forming the bile ducts) in the liver and (iii) a third group comprising bright pixels which represent all other cells in the liver. The clustering may be performed using a fuzzy-c-means clustering method, which generates a soft boundary between the different clusters.

It is noted that the amount of collagen tends to increase around sinusoidals and bile ducts in the liver. Thus, enhancing signals in the areas around the sinusoidals and bile ducts in the SHG image can facilitate subsequent extraction of finer (i.e. smaller) collagen areas with pixels having a low intensity. This enhancement of SHG signals around the sinusoidals and bile ducts is performed in step 1.2.

In step 1.2, a weight a is first assigned to each group of pixels in the TPEF image based on a probability of collagen aggregation in areas comprising the group of pixels. Thus, the weight α assigned to the group of dim pixels representing sinusoidals and bile duct cannaliculi in the liver is usually higher (e.g. the weight α assigned to this group may be a number between 40 to 100) as compared to the weights α assigned to the other groups of pixels (e.g. the weight α assigned to the remaining groups of pixels may be 1). The weight assigned to the group of dim pixels can range from 1 to 200 and preferably, ranges from 1 to 110. More preferably, the weight assigned to the group of dim pixels is 70. This is because the sensitivity of Stage 1 in identifying collagen areas decreases when the weight assigned to the group of dim pixels exceeds 70 and deteriorates further when the weight assigned to the group of dim pixels exceeds 110. The weight assigned to the other groups of pixels can range from 1 to 100 and is preferably 1. As mentioned earlier, this weight assigned to the other groups of pixels is usually smaller than the weight assigned to the group of dim pixels. Alternatively, the weights may be determined systematically using training data. In this alternative, training samples with known stages of liver fibrosis may be used as input data to method 100 and the weights may be set to maximize the differences between the quantification results obtained for samples associated with early stages of liver fibrosis and samples associated with late stages of liver fibrosis (e.g. maximize the scores shown in Table 2 for the two-channel method). A mask comprising a plurality of pixels with each pixel comprising a weight α is thus formed from the weighting of the pixels in the TPEF image. Note that if the intensity of a pixel in the SHG image exceeds a maximum allowable intensity after applying the mask to the SHG image (as will be elaborated below), the intensity of the pixel in the SHG image will be set as the maximum allowable intensity. Therefore, it is preferable to ensure that the weight assigned to the group of dim pixels is not so large that a majority of pixels in the SHG image after application of the mask have the maximum allowable intensity.

Next in step 1.2, the mask is applied to the SHG image whereby the intensity of each pixel in the SHG image is adjusted according to the weight for the corresponding pixel in the mask. This enhances the weak SHG signals in the SHG image and forms an enhanced SHG image with enhanced collagen areas (since the weights are assigned based on the probability of collagen aggregation in the areas).

In step 1.3, the enhanced SHG image is segmented to identify the collagen areas in the SHG image. In one example, an Otsu method is performed to segment the enhanced SHG image. The Otsu method is a classic global threshold algorithm which aims to find the optimal threshold that minimizes intra-class variance.

Figure 2:
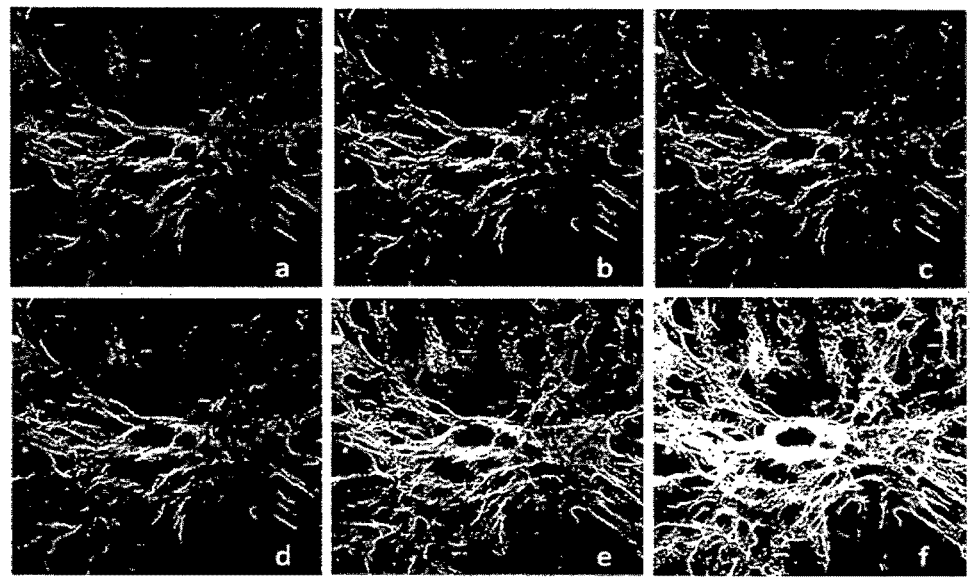

FIG. 2(*a*) illustrates an SHG image comprising liver tissue whereas FIGS. 2(*b*)-(*f*) are binary images illustrating segmentation results obtained after segmenting the SHG image of FIG. 2(*a*) using four classic segmentation methods and the two-channel method in Stage 1 as described above. The four classic segmentation methods include (i) the Otsu method [18] which is a classic global threshold algorithm that aims to find an optimal threshold that minimizes intra-class variance, (ii) the K-means [19, 20] method, (iii) the Fuzzy C-means [21] clustering method (the K-means method and the Fuzzy C-means clustering method are widely used methods for classifying observations into clusters based on how similar the observations are to one another) and (iv) the Gaussian Mixture Model (GMM) and Expectation Maximize (EM) method [22] which employs a statistic model-based approach which assumes that the histogram of the input data is a mixture of several Gaussian distributions. In the GMM and EM method, the EM method is used to estimate optimized parameters of Gaussian distributions that best fit the input data. In particular, FIGS. 2(*b*)-(*f*) respectively illustrate the segmentation results obtained using the Otsu method, the K-means clustering method, the Fuzzy-C-means clustering method, the GMM and EM method and the two-channel method employed in Stage 1 of method 100 In the binary images shown in FIGS. 2(*b*)-(*f*), the white pixels represent the segmented collagen areas and the black pixels represent the background of the SHG image. It can be seen that the collagen areas segmented using different algorithms comprise different amounts of collagen. For example, the binary image in FIG. 2(*f*) corresponding to the two-channel method of method 100 includes areas of fine collagen not visible in the other binary images in FIGS. 2(*b*)-2(*e*).

Figure 3:
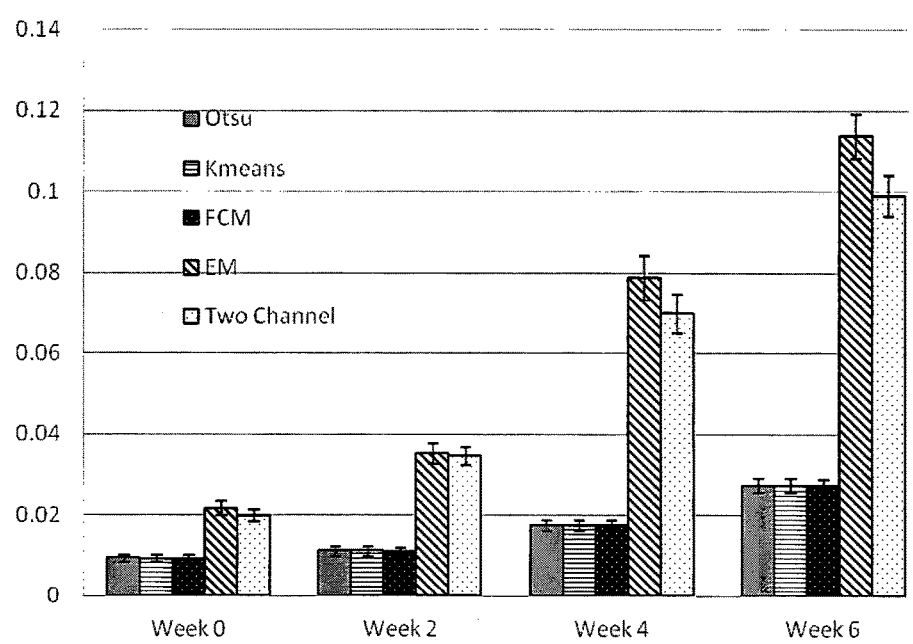
FIG. 3 illustrates a histogram plotting fraction of collagen identified in input samples using different segmentation methods and a two-channel method used in a stage in the method of FIG. 1 against stages of fibrosis associated with the input samples.

FIG. 3 shows a histogram illustrating collagen areas segmentation results obtained using the four classic segmentation methods as mentioned above and the two-channel method used in Stage 1 of method 100 These results are obtained for a data set comprising a plurality of input samples. In FIG. 3, the samples are grouped based on their pathology scores (i.e. stages of fibrosis). The x-axis of FIG. 3 indicates the pathology scores associated with the samples whereas the y-axis indicates the fraction of collagen in the samples (i.e. the number of pixels in the segmented collagen areas in the SHG image divided by the total number of pixels in the liver tissue in the TPEF image).

Note that the results in FIG. 3 are obtained based on the collagen areas segmented from the entire liver tissue comprised in the input data. It is possible for the EM method to segment a greater amount of collagen from the entire liver tissue as compared to the two-channel method. For example, FIG. 3 shows that the fraction of collagen segmented by the EM method is higher than that by the two-channel method. However, this does not necessarily mean that the EM method performs better than the two-channel method. This is because there is a possibility that noise pixels with a relatively high intensity are wrongly segmented as collagen pixels using the EM method. A more accurate indicator of the performance of the segmentation methods is the AUROC value as will be elaborated below. On the other hand, FIGS. 2(*a*)-2(*f*) show that the amount of collagen segmented by the two-channel method is greater than that of the EM method. This is because FIGS. 2(*a*)-2(*f*) illustrate only a portion of the liver tissue comprising a large amount of bile duct cells where the probability of collagen aggregation is higher. In other words, most of the pixels in FIG. 2(*f*) represent collagen corresponding to pixels with a higher weight in the mask formed in step 1.2. Thus, FIG. 2(*f*) is a better indicator of the ability of the two-channel method in extracting finer collagen areas found around the bile duct cells.

An area under a receiver operating characteristic curve (AUC or AUROC) [23] for the different segmentation methods may be used as a statistic to evaluate the performance of these segmentation methods. The AUC or AUROC for the different segmentation methods are shown in Table 2. In. Table 2, the AUC or AUROC is shown in the columns headed by the names of the segmentation methods. These scores indicate the ability of the segmentation methods in differentiating between the stages of fibrosis shown in the leftmost column. A larger score indicates a higher ability in differentiating the stages of fibrosis. From Table 2, it can be seen that the two-channel method used in Stage 1 of method 100 achieves the best performance in most cases. Note that generally, the segmentation methods fare worst in differentiating between stages 1 and 2 of fibrosis as shown in Table 1. This is because there is usually little difference in the collagen percentage present during stages 1 and 2 of fibrosis since collagen proliferation only accelerates after stage 2 or 3 of fibrosis. Furthermore, the results in Table 1 were obtained using a small sample size for stage 1 of fibrosis. This leads to a higher variation in the samples with stage 1 of fibrosis, in turn resulting in a higher difficulty in separating the samples with stages 1 and 2 of fibrosis.

TABLE 2

| Differentiated stages of fibrosis | Otsu method | GMM and EM method | Kmeans clustering method | Fuzzy C-Means clustering method | Two-Channel method used in stage 1 of method 100 |
|---|---|---|---|---|---|
| 0 vs. 1 | 0.772321 | 0.879464 | 0.772321 | 0.785714 | 0.925926 |
| 1 vs. 2 | 0.333333 | 0.451389 | 0.333333 | 0.319444 | 0.394231 |
| 2 vs. 3 | 0.767196 | 0.800705 | 0.775132 | 0.773369 | 0.865878 |
| 3 vs. 4 | 0.60352 | 0.653209 | 0.590062 | 0.615942 | 0.671329 |

Stage 2: Identifying Normal Collagen Areas and Abnormal Collagen Areas in the SHG Image In Stage 2 of method 100, the segmented collagen areas in the SHG image obtained from Stage 1 are divided into two groups: one group comprising large patches of collagen areas which may be located around blood vessels and bile ducts (in other words, areas comprising aggregated collagen or normal collagen) and another group comprising finer collagen areas which may be distributed in sinusoidal regions or between different portal tracts (in other words, areas comprising distributed collagen or abnormal collagen). Abnormal collagen is indicative of fibrosis whereas normal collagen can also be found in healthy samples and thus, does not accurately reflect the progression of fibrosis (i.e. is not indicative of fibrosis). Therefore, it is preferable to identify the areas comprising normal collagen before proceeding with the generation of measurements using the collagen areas. Thus, in Stage 2 of method 100, the identified collagen areas in the SHG image are divided into areas comprising normal collagen (normal collagen areas) and areas comprising abnormal collagen (abnormal collagen areas). This is performed using steps 2.1-2.6 as follows.

In step 2.1, the same sub-steps performed in step 1.1 of Stage 1 are performed to identify a group of pixels representing lumens in the TPEF image. More specifically, pixels in the TPEF image are segmented into different groups based on their intensities whereby one of these groups of pixels represents lumens in the TPEF image. In one example, the pixels in the TPEF image are segmented into 3 different groups: (i) a first group comprising completely dark pixels which represent areas of vessels and spaces outside the liver tissue, (ii) a second group comprising dim pixels which represent sinusoidals and bile duct cannaliculi (forming the bile ducts) in the liver and (iii) a third group comprising bright pixels which represent all other cells in the liver. The first group of pixels comprising completely dark pixels are identified as the group of pixels representing lumens in the TPEF image. The clustering may be performed using a fuzzy-c-means clustering method, which generates a soft boundary between the different clusters. Alternatively, segmentation of the pixels in the TPEF image is not performed in step 2.1 and the segmented TPEF image from step 1.1 of Stage 1 may be used to identify the group of pixels representing lumens in the TPEF image.

In steps 2.2-2.4, boundary pixels of lumens (i.e. pixels belonging to the boundaries of lumens) in the TPEF image are identified. In step 2.2, an initial mask is formed from the segmented TPEF image by setting the group of pixels representing the lumens as foreground pixels and the remaining pixels as background pixels. Holes in areas formed by the foreground pixels in the initial mask are then filled by performing a morphological reconstruction operation [24] on the initial mask. In one example, the morphological reconstruction identifies connected background pixels in the initial mask and converts these connected background pixels to foreground pixels. The morphological reconstruction begins with a set of starting background pixels and grows this set of starting background pixels in a flood-filled fashion to include connected pixels of the starting background pixels. More specifically, the morphological reconstruction starts by generating a first set of connected pixels of the starting background pixels whereby this first set of connected pixels comprises the immediate neighbours (e.g. 4-neighbour pixels) of the starting background pixels. The morphological reconstruction then adds to this first set of connected pixels immediate neighbours of this first set of connected pixels (in other words, further neighbours of the starting background pixels) to form a second set of connected pixels. The same is done for the second set of connected pixels and so on. This addition of pixels to the set of connected pixels continues until the most recently added pixels comprise one or more pixels corresponding to pixels along boundaries in the mask. These boundaries are boundaries of unfilled lumens in the mask and comprise foreground pixels (since the unfilled lumens are represented by areas formed by the foreground pixels in the mask). In other words, the addition of pixels to the set of connected pixels continues until the most recently added pixels comprise one or more pixels which are foreground pixels. The background pixels in the final set of connected pixels, together with the starting background pixels, are then converted to foreground pixels.

Next in step 2.3, a morphological erosion is performed on the mask to remove foreground pixels corresponding to pixels along object boundaries in the segmented TPEF image. The foreground pixels are removed by converting these foreground pixels into background pixels. In a typical morphological erosion, the number of pixels removed usually depends on the size and shape of the structuring element (usually a simple, pre-defined shape) used for the morphological erosion as the structuring element defines the neighbourhood of interest of each pixel. In step 2.3, the structuring element may be a diamond, a rectangle or a square and the radius or width (whichever is applicable) of the structuring element may range from 1 to 5 pixels. More specifically, in the morphological erosion performed in step 2.3, the mask is probed with the structuring element to determine how the structuring element fits shapes formed by the foreground pixels in the mask. This is performed by placing a center of the structuring element over each foreground pixel in the mask. If the entire structuring element overlaps with the foreground pixels in the mask, the foreground pixel (on which the center of the structuring element is) is retained. On the other hand, if only a part of the structuring element overlaps with the foreground pixels in the mask, the foreground pixel (on which the center of the structuring element is) is converted to a background pixel. In other words, the erosion can be understood as a locus of points reached by the center of the structuring element (which is located on the origin of the image space) as the structuring element moves inside the mask.

A new mask comprising a plurality of foreground pixels is thus formed from the morphological reconstruction and erosion performed in steps 2.2 and 2.3. In step 2.4, this new mask is subtracted pixel-by-pixel from the initial mask (formed in step 2.2) to form a difference mask. The difference mask indicates the locations of boundary pixels of lumens in the TPEF image, thus identifying the boundary pixels of lumens in the TPEF image. Boundary pixels of lumens in the SHG image are then located using these identified boundary pixels of lumens in the TPEF image, more specifically, using the difference mask.

In step 2.5, a region growing method is performed on the pixels in the segmented SHG image (in other words, the binary image obtained after segmenting the SHG image in step 1.3 of Stage 1). In one example, the region growing method is performed using a set of pixels called a "normal collagen set". The normal collagen set is first set as a null set. The located boundary pixels of lumens obtained from step 2.4 are set as starting pixels. For each starting pixel, beginning from the immediate neighbour pixels (e.g. the 4-neighbour pixels (for a 2D SHG image)) of the starting pixel, if the immediate neighbour pixels are comprised in the collagen areas identified in Stage 1, the immediate neighbour pixels are added to the normal collagen set. Next, further neighbour pixels of the starting pixel are evaluated and if the further neighbour pixels are comprised in the collagen areas identified in Stage 1, the further neighbour pixels are added to the normal collagen set. This addition of further neighbour pixels to the normal collagen set is repeated until the number of newly added pixels to the normal collagen set is smaller than the number of pixels added to the normal collagen set in the first iteration (i.e. the number of immediate neighbour pixels added to the normal collagen set). Thus, in step 2.5, pixels in the SHG image which belong to the identified collagen areas and which are neighbouring the located boundary pixels of lumens are located.

Subsequently in step 2.6, pixels in the normal collagen set are classified as pixels belonging to the normal collagen areas whereas the remaining pixels in the identified collagen areas are classified as pixels belonging to abnormal collagen areas. Thus, the identified collagen areas in the SHG image are divided into normal collagen areas and abnormal collagen areas.

Figure 4:
FIG. 4 illustrates an example segmented SHG image comprised in input data to the method of FIG. 1, whereby the example segmented SHG image comprises segmented normal collagen areas and segmented abnormal collagen areas.

FIG. 4 shows an example segmented SHG image (in other words, the binary image after segmentation of the SHG image in Stage 1) with segmented normal collagen areas and segmented abnormal collagen areas. More specifically, in FIG. 4, the gray areas (for example, area 502) represent the normal collagen areas whereas the white areas (for example, area 504) represent the abnormal collagen areas.

Figure 5:
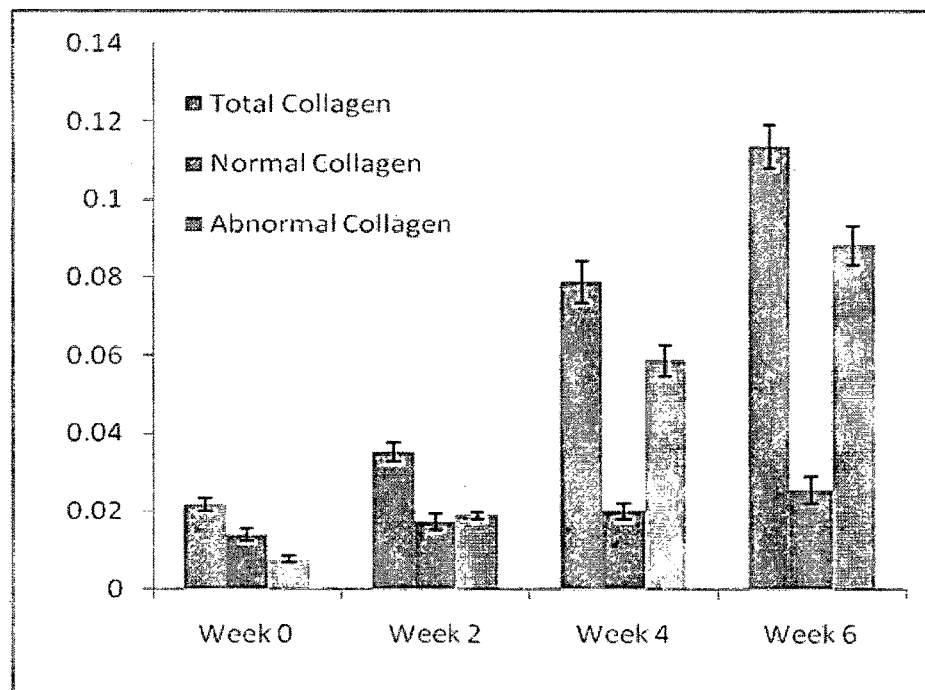
FIG. 5 illustrates a histogram plotting fraction of total collagen, fraction of normal collagen and fraction of abnormal collage identified in input samples using a stage in the method of FIG. 1 after different weeks of fibrosis progression.

FIG. 5 shows a histogram illustrating quantification results obtained by applying Stage 2 of method 100 on a data set comprising input samples. The x-axis of the histogram in FIG. 5 indicates fibrosis progression whereas the y-axis indicates the fraction of total collagen (i.e. the number of pixels in the identified collagen areas in the SHG image divided by the number of pixels in the liver tissue in the TPEF image), the fraction of normal collagen (i.e. the number of pixels identified as belonging to normal collagen areas in the SHG image divided by the number of pixels in the liver tissue in the TPEF image) and the fraction of abnormal collagen (i.e. the number of pixels identified as belonging to abnormal collagen areas in the SHG image divided by the number of pixels in the liver tissue derived from the TPEF image) found in the input samples after different weeks of fibrosis progression indicated on the x-axis. As shown in FIG. 5, as the fibrosis progresses, the fraction of normal collagen does not change by a substantial amount whereas the fraction of abnormal collagen changes substantially.

Stage 3: Identifying Portal Tracts and Central Veins in the TPEF Image

In Stage 3 of method 100, portal tracts and central veins are identified using the TPEF image. As shown in FIG. 1, Stage 3 comprises steps 3.1, 3.2, 3.3 and 3.4 as will be described in more detail below.

In step 3.1, lumens in the TPEF image are first identified using the same steps as in step 1.1. More specifically, the pixels in the TPEF image are segmented into different groups based on their intensities. One of these groups is a group of pixels representing the lumens in the TPEF image. In one example, the pixels in the TPEF image are segmented into 3 different groups: (i) a first group comprising completely dark pixels which represent areas of vessels and spaces outside the liver tissue, (ii) a second group comprising dim pixels which represent sinusoidals and bile duct cannaliculi (forming the bile ducts) in the liver and (iii) a third group comprising bright pixels which represent all other cells in the liver. The first group of pixels comprising completely dark pixels are identified as the group of pixels representing lumens in the TPEF image. The clustering may be performed using a fuzzy-c-means clustering method, which generates a soft boundary between the different clusters. Alternatively, segmentation of the pixels in the TPEF image is not performed in step 3.1 and the segmented TPEF image from step 1.1 of Stage 1 may be used to identify the lumens in the TPEF image.

Next in step 3.2, morphological features of each identified lumen in the TPEF image such as its area, convex area, eccentricity, major axis length, minor axis length and/or solidity are extracted. A k-means clustering method is then performed using these extracted morphological features to classify the identified lumens into two groups: one group comprising lumens with regular shapes and the other group comprising lumens with irregular shapes. The lumens with irregular shapes are excluded from further analysis.

In step 3.3, denoting each regular-shaped lumen as a node in the TPEF image, a graph is generated from the nodes based on the Delaunay triangulation using Qhull method [25]. This method generates a set of lines connecting each node to its natural neighbouring nodes. Spatial texture features of each node, such as those based on the generated set of lines connected to the node (e.g. the average and/or standard deviation of the number of pixels lying along the lines) are extracted. Based on these extracted spatial texture features, a k-means clustering method is performed to cluster the regular-shaped lumens to locate groups of clustered lumens. Then, it is determined whether each regular-shaped lumen belongs to a group of clustered lumens. If not, the regular-shaped lumen is classified as a separated lumen. Each group of clustered lumens is then identified as a portal tract whereas each separated lumen is identified as a central vein.

In step 3.4, regions of interest i.e. portal tract regions and central vein regions are identified. In step 3.4, a voronoi polygon is first generated for each node using the Qhull method [25]. This is performed by generating a polygon that encloses all the intermediate nodes that are closer to the node than to other nodes in the TPEF image. The region in the polygon is identified as a portal tract region if the polygon is generated for a node denoting a lumen belonging to a group of clustered lumens and is identified as a central vein region if the polygon is generated for a node denoting a separated lumen.

Figure 6:
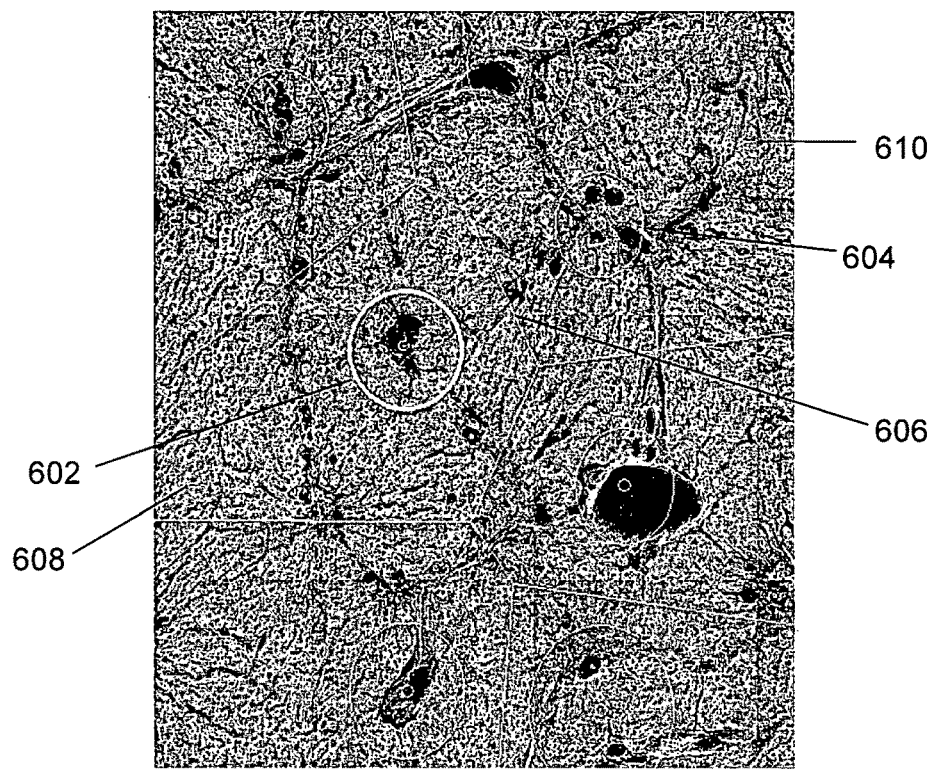
FIG. 6 illustrates an image showing information in both a Two-Photon Excitation Fluorescence (TPEF) channel and a SHG channel comprised in input data to the method of FIG. 1 whereby the image comprises identified portal tracts, central veins, portal tract regions and central vein regions.

FIG. 6 shows an image showing information in both the TPEF channel and the SHG channel of the input data with identified portal tracts, central veins, portal tract regions and central vein regions. Circle 602 encloses an example central vein whereas circle 604 encloses an example portal tract. The lines in between the circles (e.g. line 606) form the outlines of the voronoi polygons. The region 608 is an example central vein region whereas the region 610 is an example portal tract region.

Stage 4: Generate Measurements Using the Identified Collagen Areas, Normal Collagen Areas, Abnormal Collagen Areas, Portal Tracts and Central Veins In Stage 4, to quantify liver fibrosis progression of the liver in the input data, a plurality of measurements relating to histo-pathological features [1] shown in Table 3 are generated based on the morphological features identified in the earlier stages of method 100, in particular, the identified collagen areas, normal collagen areas, abnormal collagen areas, portal tracts and central veins.

TABLE 3

| Hepatocellular changes | Inflammation | Biliary changes | Fibrosis and architecture changes |
|---|---|---|---|
| Ballooning degeneration | Portal | Bile duct injury | Quantity of fibrous tissue |
| Acidophilic degeneration/ apoptosis | Periportal (interface hepatitis) | Ductular reaction | Location (portal, perisinusoidal, speta and nodule formation) |
| Dropout/confluent necrosis | Lobular | Ductopenia | |
| Mallory bodies | Intravascular (endotheliitis) | | |
| Steatosis | Kupffer cell hypertrophy | | |
| Iron storage | Granulomas | | |
| Bile stasis | | | |
| Cholate stasis | | | |

Measurements relating to fibrosis and architecture changes in the liver may be generated and these include:

1) Total amount of collagen relative to total amount of liver tissue in the liver:

This may be expressed as the fraction (or percentage) of collagen present in the liver and may be calculated as the number of pixels belonging to the collagen areas identified in the SHG image (in Stage 1) divided by the number of pixels belonging to the liver tissue in the TPEF image.

2) Amount of normal collagen relative to total amount of liver tissue in the liver;

This may be expressed as the fraction (or percentage) of normal collagen (comprising collagen aggregated around lumens) in the liver and may be calculated as the number of pixels belonging to normal collagen areas identified in the SHG image (in Stage 2) divided by the number of pixels belonging to the liver tissue in the TPEF image.

3) Amount of abnormal collagen relative to total amount of liver tissue in the liver;

This may be expressed as the fraction (or percentage) of abnormal collagen (comprising distributed collagen) in the liver and may be calculated as the number of pixels belonging to abnormal collagen areas identified in the SHG image (in Stage 2) divided by the number of pixels belonging to the liver tissue in the TPEF image;

4) Collagen amount in portal tracts relative to total amount of liver tissue in the liver;

This may be expressed as the fraction (or percentage) of collagen in the portal tracts of the liver and may be calculated as the number of pixels belonging to collagen areas in portal tracts divided, by the number of pixels belonging to the liver tissue in the TPEF image. The collagen areas in portal tracts may be identified by applying the SHG image comprising identified collagen areas (obtained in Stage 2) to the TPEF image comprising identified portal tracts (obtained in Stage 3) or vice versa.

5) Portal tracts bridging index

This is a measurement based alone on the portal tracts and central veins identified in Stage 3 of method 100. This measurement may be expressed as the fraction (or percentage) of the identified portal tracts which have bridged to other identified portal tracts or identified central veins. To determine if a portal tract has bridged to other portal tracts or central veins, the pixels belonging to each portal tract are examined. If at least one pixel belonging to a portal tract also belongs to at least one other portal tract or central vein, it is determined that this portal tract has bridged to other portal tracts or central veins.

Figure 7:
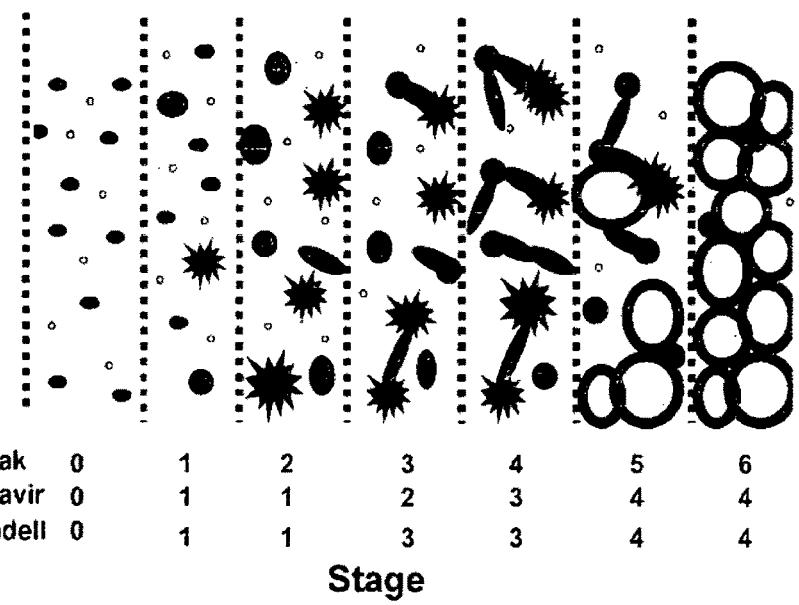
FIG. 7 illustrates a diagrammatic representation of architecture changes in the liver occurring at different stages of fibrosis.

FIG. 7, taken from [1], shows a diagrammatic representation of architecture changes in the liver occurring at different stages of fibrosis. In FIG. 7, the 7 stages (stages 0-6) of the Ishak fibrosis score is compared against the 5 stages (stages 0-4) of the Metavir fibrosis score and the 3 stages (stages 1, 3 and 4) of the Knodell score. As shown in FIG. 7, one of the significant collagen architecture changes during the early stages of fibrosis is portal expansion which is shown in FIG. 7 by the increasing sizes of the black dots and the transformation of the black dots to black star-like patterns as fibrosis progresses in the early stages. Thus, the amount of abnormal collagen and the collagen amount in portal tracts tend to be good measurements for identifying early stages of fibrosis. On the other hand, the portal tracts bridging index is a good measurement for identifying mid to late stages of fibrosis as bridging of the portal tracts to other portal tracts or central veins is usually one of the significant collagen architecture changes during these stages of fibrosis.

Measurements relating to biliary changes in the liver may optionally be generated in Stage 4 of method 100 and may include:

Amount of bile duct cell proliferation relative to total amount of liver tissue in the liver This may be expressed as the fraction (or percentage) of bile duct cells in the liver.

The following steps may optionally be included in method 100 for identifying bile duct cells prior to Stage 4 and for generating the amount of bile duct cell proliferation in Stage 4. The bile duct cells in the TPEF image may be identified prior to Stage 4 by segmenting the TPEF image to form a mask of segmented bile duct cells. This may be performed using a fuzzy-c-means clustering method (same as the method used in step 3.1). The amount of bile duct cell proliferation may then be calculated in Stage 4 as the number of pixels belonging to the segmented bile duct cells in the mask divided by the number of pixels belonging to liver tissue in the TPEF image.

Figure 8:
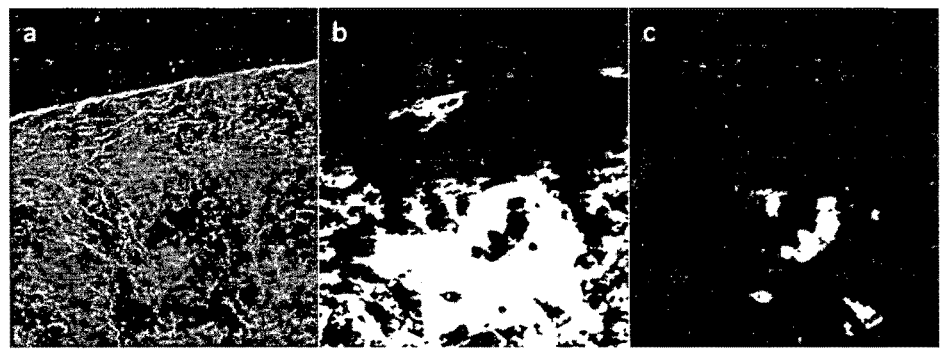
FIG. 8(a) illustrates an example TPEF image comprised in input data to the method of FIG. 1.
FIG. 8(b) illustrates a mask of segmented bile duct cells obtained from the example TPEF image of FIG. 8(a)
FIG. 8(c) illustrates a mask of segmented dying hepatocytes obtained from the example TPEF image of FIG. 8(a) and the mask of segmented bile duct cells of FIG. 8(b)
Figure 9:
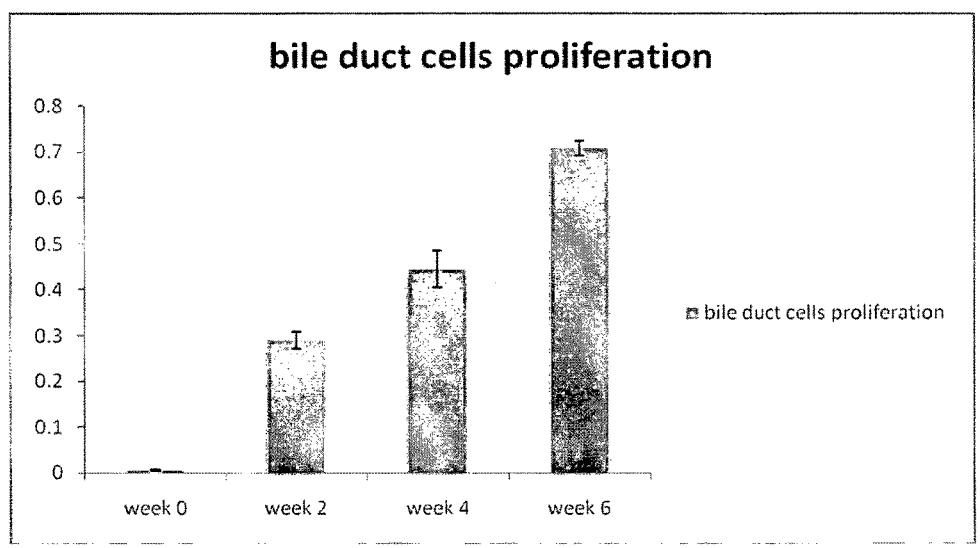
FIG. 9 illustrates a histogram plotting an amount of bile duct cell proliferation identified in input samples using a stage in the method of FIG. 1 after different weeks of fibrosis progression.

FIG. 8(*a*) shows an example TPEF image whereas FIG. 8(*b*) shows a mask of segmented bile duct cells whereby the mask is formed by segmenting the TPEF image in FIG. 8(*a*). FIG. 9 shows a histogram illustrating quantification results obtained for a plurality of input samples in a data set. The histogram in FIG. 9 is a plot of the amount of bile duct cell proliferation in the input samples after different weeks of fibrosis progression. As shown in FIG. 9, the amount of bile duct cell proliferation increases with the progression of fibrosis.

Measurements relating to hepatocellular changes in the liver may also optionally be generated in Stage 4 of method 100 and may include:

Amount of dying hepatocytes relative to total amount of liver tissue in the liver This may be expressed as the fraction (or percentage) of dying hepatocytes in the liver.

The following steps may optionally be included in method 100 for identifying hepatocytes and dying hepatocytes prior to Stage 4 and for generating the amount of dying hepatocytes relative to the total amount of liver tissue in the liver in Stage 4. Dying hepatocytes may be defined as hepatocytes surrounded by bile duct cells. In one example, the dying hepatocytes are identified prior to Stage 4 by first segmenting the TPEF image to form a mask of segmented hepatocytes. This may be performed using a fuzzy-c-means clustering method (same as the method used in step 3.1). A mask of segmented bile duct cells is then obtained using for example the steps mentioned above with respect to calculating the amount of bile duct cell proliferation. Holes in the mask of segmented bile duct cells are then filled using a morphological reconstruction operation (similar to the operation performed in Stage 2). This forms a filled mask whereby holes within a ring of segmented bile duct cells are also filled. The mask of segmented hepatocytes is then multiplied pixel by pixel with the filled mask to form a mask of dying hepatocytes. The purpose of this multiplication is to identify segmented hepatocytes which overlap the filled holes within rings of segmented bile duct cells i.e. segmented hepatocytes surrounded by segmented bile duct cells. These segmented hepatocytes which overlap the filled holes within rings of segmented bile duct cells are represented by pixels with non-zero values in the mask of dying hepatocytes and are identified as the dying hepatocytes. The fraction of dying hepatocytes in the input data may then be calculated in Stage 4 as the number of pixels belonging to the dying hepatocytes in the mask of dying hepatocytes divided by the number of pixels belonging to the liver tissue in the TPEF image.

Figure 10:
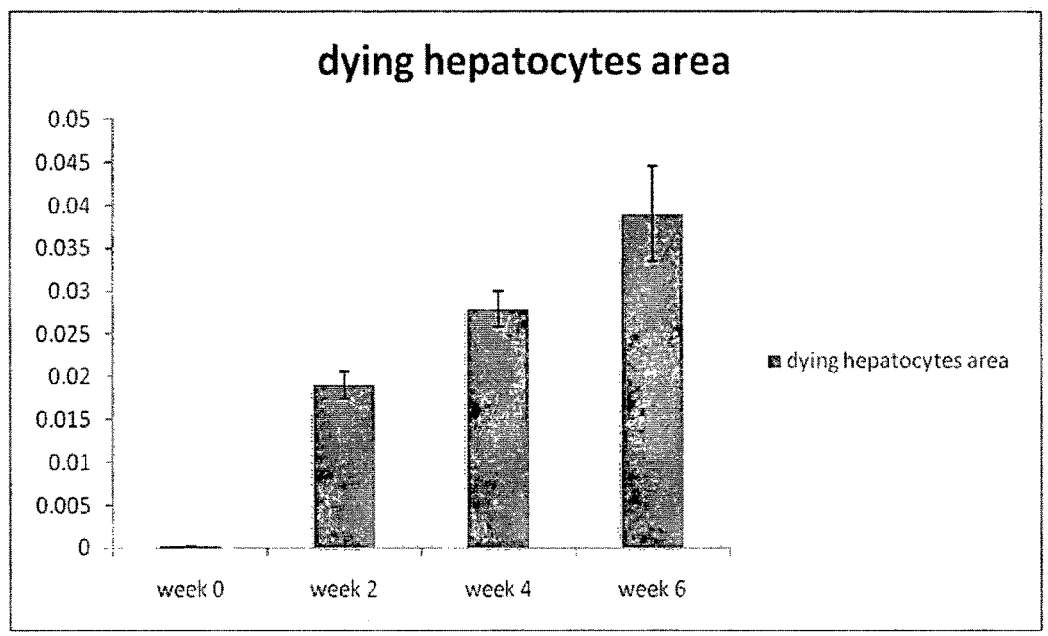
FIG. 10 illustrates a histogram plotting a fraction of dying hepatocytes identified in input samples using a stage in the method of FIG. 1 after different weeks of fibrosis progression.

FIG. 8(*c*) shows a mask of dying hepatocytes whereby the mask is obtained from the TPEF image of FIG. 8(*a*) and the mask of FIG. 8(*b*). FIG. 10 shows a histogram illustrating quantification results obtained for a plurality of input samples in a data set. The histogram in FIG. 10 is a plot of the fraction of dying hepatocytes in the input samples after different weeks of fibrosis progression as indicated on the x-axis of the histogram. As shown in FIG. 10, the fraction of dying hepatocytes increases with the progression of fibrosis.

Further measurements relating to other histo-pathological features shown in Table 3 may also be made in method 100. For example, inflammatory cells may be identified and measurements may be generated based on these inflammatory cells.

Stage 5: Determining a Stage of Fibrosis in the Liver Based on the Generated Measurements In Stage 5, a stage of fibrosis in the liver is determined (or predicted) based on the generated measurements. This may be performed using a computer-aided diagnosis (CAD) system. The predicted stage of fibrosis in the liver may be automatically generated using supervised machine learning algorithms (such as neural network, support vector machine, classification tree) or unsupervised clustering algorithms. The term "automatically" is used here to mean that, although human interaction may initiate the algorithm, human interaction is not required while the algorithm is carried out.

For supervised machine learning algorithms, a training set comprising a plurality of training samples with known pathology scores (i.e. known stages of liver fibrosis) is usually required. Each training sample comprises input data relating to a liver comprising liver tissue. Taking a neural network as an example, the neural network may be trained (for example, by adjusting the weights of the neural network) with measurements generated from the training samples using method 100 and the known pathology scores of these training samples. To determine a stage of fibrosis in a patient's liver, a set of measurements is generated from input data relating to the patient's liver using method 100 and is then processed via the trained neural network to obtain a stage of fibrosis for the patient's liver. The performance of a trained supervised machine learning algorithm may be tested using a data set comprising a further plurality of training samples with known pathology scores. After inputting measurements generated from the further plurality of training samples into the trained supervised machine learning algorithm, a predicted pathology score is produced for each training sample and is compared against the ground-truth (i.e. the known pathology score).

The advantages of the embodiments of the present invention are as follows:

In the embodiments of the present invention, a plurality of measurements based on a plurality of identified morphological features is used to determine a stage of fibrosis in a liver. This is advantageous over prior art methods which use fibrosis area as the only measurement for determining the stage of fibrosis, since there is also a strong correlation between other pathological features (such as fibrosis architecture changes) and the stage of fibrosis. Thus, these other pathological features can also influence the accuracy in the grading and staging of fibrosis [2] and it is preferable to consider these other pathological features as well. Furthermore, although collagen percentage closely correlates to the severity of liver fibrosis, it has its limitations (for example, even the existing gold standard may not be accurate in determining the severity of liver fibrosis). On the other hand, the embodiments of the present invention advantageously include additional architectural information (such as portal tract location, structure and spacing) by identifying and quantifying features from this additional architectural information to stage liver fibrosis. Note that the additional architectural information may be obtained from any part of the liver, for example, at the surface, in the capsular region, in the sub-capsular region or in deeper regions of the liver. Since the sub-capsular region is close to the capsular region which is located at the liver surface and architectures such as the portal tracts are normally not located at the liver surface, the locations of collagen areas in the sub-capsular region may not be easily found. Using the embodiments of the present invention which employ architectural information other than locations of collagen areas or portal tracts, the sub-capsular region of the liver may also be examined.

Furthermore, the embodiments of the present invention comprise a quantification system for staging liver fibrosis automatically in an animal model. Computer-aided systems may be implemented in the embodiments of the present invention to process the multiple measurements using for example, supervised machine learning algorithms or unsupervised clustering algorithms.

The embodiments of the present invention can be used on images of the liver regardless of whether they are images of the interior or the surface of the liver. In addition, the embodiments of the present invention use information in both the TPEF and SHG channels. This is advantageous over prior art methods which use information in the SHG channel only. This can be seen from Table 2 which shows that the two-channel method used in Stage 1 of method 100 performs better than other classic segmentation techniques in segmenting collagen areas.

REFERENCES

1. D. Goodman, Z., *Grading and staging systems for inflammation and fibrosis in chronic liver diseases*. Journal of Hepatology, 2007. 47: p. 598-607.
2. Standish, R. A., et al., *An appraisal of the histopathological assessment of liver fibrosis*. Gut, 2006. 55: p. 569-578.
3. Knodell, R., et al., *Formulation and application of a numerical scoring system for assessing histological activity in asymptomatic chronic active hepatitis*. Hepatology, 1981. 1(5): p. 431-5.
4. Scheuer, P., *Classification of chronic viral hepatitis: a need for reassessment* Journal of Hepatology, 1991. 13: p. 372-4.
5. Ishak, K., et al., *Histological grading and staging of chronic hepatitis*. Journal of Hepatology, 1995. 22(6): p. 696-9.
6. Bedossa, P. and T. Poynard, *The METAVIR cooperative study group. An algorithm for the grading of activity in chronic hepatitis C*. Journal of Hepatology, 1996. 24(289-93).
7. Bedossa, P., et al., *Intraobserver and interobserver variations in liver biopsy interpretation in patients with chronic hepatitis C. The French METAVIR Cooperative Study Group*. Hepatology, 1994. 20(1): p. 15-20.
8. Gronbaek, K., et al., *Interobserver variation in interpretation of serial liver biopsies from patients with chronic hepatitis C*. Journal of Viral Hepatitis, 2002. 9(6): p. 443-449.
9. Westin, J., et al., *Interobserver study of liver histopathology using the Ishak score in patients with chronic hepatitis C virus infection*. Liver, 1999. 19(3): p. 183-187.
10. Masseroli, M., et at., *Automatic quantification of liver fibrosis: design and validation of a new image analysis method: comparison with semi-quantitative indexes of fibrosis*. Journal of Hepatology, 2000. 32(3): p. 453-64.
11. O'Brien, M., et al., *An assessment of digital image analysis to measure fibrosis in liver biopsy specimens of patients with chronic hepatitis C*. American Journal of Clinical Pathology, 2000. 114(5): p. 712-8.
12. Wright, M., et al., *Quantitative versus morphological assessment of liver fibrosis: semi-quantitative scores are more robust than digital image fibrosis area estimation*. Liver International, 2003. 23(1): p. 28-34.
13. Lazzarini, A. L., et al., *Advances in digital quantification technique enhance discrimination between mild and advanced liver fibrosis in chronic hepatitis C*. Liver International, 2005. 25: p. 1142-1149.
14. Friedenberg, M. A., et al., *Simplified method of hepatic fibrosis quantification: design of a new morphometric analysis application*. Liver International, 2005. 25: p. 1156-1161.
15. Matalka, I. I. O. M. Al-Jarrah, and T. M. Manasrah, *Quantitative assessment of liver fibrosis: a novel automated image analysis method*. Liver International, 2006 (26): p. 1054-1064.
16. Goodman, Z. D., et al., *Progression of Fibrosis in Advanced Chronic Hepatitis C: Evaluation by Morphometric Image Analysis*. Hepatology, 2007. 45(4): p. 886-94.
17. Dioguardi, N., et al., *Metrically measuring liver biopsy: A chronic hepatitis B and C computer-aided morphologic description*. World Journal of Gastroenterology, 2008. 14(48): p. 7335-7344.
18. Otsu, N., *A Threshold Selection Method from Gray-Level Histograms*. Systems, Man and Cybernetics, IEEE Transactions on, 1979. 9(1): p. 62-66.
19. P.Lloyd, S., *Least Squares Quantization in PCM*. IEEE TRANSACTIONS ON INFORMATION THEORY, 1982. 28(2): p. 129-137.
20. Shapiro, L. G. and G. C. Stockman, *Computer Vision*. 2001: Upper Saddle River, N.J.: Prentice Hall.
21. Bezdek, J. C., *Pattern Recognition with Fuzzy Objective Function Algorithms*. 1981.
22. Dempster, A. P., N. M. Laird, and D. B. Rubin, *Maximum Likelihood from Incomplete Data via the EM algorithm*. Journal of the Royal Statistical Society, 1977. Series B,39(1): p. 1-38.
23. D. M. Green and J. M. Swets (1966). *Signal detection theory and psychophysics*. New York: John Wiley and Sons Inc.
24. Luc Vincent: Morphological grayscale reconstruction in image analysis: applications and efficient algorithms, IEEE Trans. on Image Processing, Vol. 2, No. 2, pp. 176-201, April 1993.
24. R. Gonzalez and R. Woods *Digital Image Processing*, Addison-Wesley Publishing Company, 1992, pp 518, 512, 550.
25. Barber, C. B., Dobkin, D. P., and Huhdanpaa, H. T., "The Quickhull algorithm for convex hulls," *ACM Trans. on Mathematical Software*, 22(4):469-483, December 1996.

What is claimed is:

1. A computerized method for determining a stage of fibrosis in a liver, the method comprising performing:

operation (1a) of receiving input image data relating to the liver, the input image data comprising a first image in a Two-Photon Excitation Fluorescence (TPEF) channel and a second image in a Second Harmonic Generation (SHG) channel, wherein the first and second images relate to a tissue structure in the liver and information relating to collagen content in the liver;

operation (1b) of identifying a plurality of morphological features of the liver from the first and second images of the input image data relating to the liver, said morphological features comprising collagen areas, operation (1b) further comprising:

segmenting a plurality of image pixels in the first image into different groups of image pixels based on intensities of the plurality of image pixels;

forming a mask by assigning a weight to each group of image pixels in the first image based on a probability of collagen aggregation in areas comprising the each group of image pixels, wherein each mask pixel comprises one of the assigned weights;

applying the mask to the second image to form an enhanced second image with enhanced collagen areas; and segmenting the enhanced second image with the enhanced collagen areas to identify the collagen areas in the second image and to thereby perform said identifying of the plurality of morphological features comprising the identified collagen areas;

operation (1c) of generating a plurality of measurements based on the identified plurality of morphological features; and operation (1d) of automatically determining the stage of fibrosis in the liver based on the generated plurality of measurements.

2. A method according to claim 1, wherein the plurality of morphological features further comprises one or more of the following groups:
group (i) comprising portal tracts and central veins; and
group (ii) comprising one or more of hepatocytes, bile duct cells, and inflammatory cells.

3. A method according to claim 2, wherein the identified plurality of morphological features comprises the portal tracts and the central veins, and wherein the generated plurality of measurements comprises a measurement based alone on the identified portal tracts and the identified central veins, and the collagen areas are portal tracts.

4. A method according to claim 3 wherein the measurement based alone on the identified portal tracts and at least one of the identified central veins is a portal tract bridging index indicating a percentage of the identified portal tracts which have bridged to other identified portal tracts or the identified central veins.

5. A method according to claim 2, wherein the identified plurality of morphological features comprises the hepatocytes and the bile duct cells, and wherein the plurality of measurements further comprises measurements relating to one or more of the following:
a total amount of collagen in the identified collagen areas;
an amount of collagen not indicative of fibrosis in the identified collagen areas;
an amount of bile duct cell proliferation generated based on the identified bile duct cells; and
an amount of dying hepatocytes generated based on the identified bile duct cells and the identified hepatocytes.

6. A method according to claim 2, wherein operation (1b) further comprises:
segmenting bile duct cells in the first image of the input image data of the liver;
segmenting hepatocytes in the first image of the input image data of the liver; and
identifying segmented hepatocytes surrounded by the segmented bile duct cells as dying hepatocytes.

7. A method according to claim 1, wherein the plurality of measurements further comprises measurements relating to one or more of the following:
an amount of collagen indicative of fibrosis in the identified collagen areas; and
an amount of collagen in portal tracts identified in the plurality of morphological features.

8. A method according to claim 1, wherein the different groups of image pixels in the first image comprise a group of image pixels representing sinusoidals and bile duct cannaliculi in the liver and the weight assigned to said group of image pixels representing the sinusoidals and bile duct cannaliculi in the liver is higher as compared to the weights assigned to other ones of the different groups of image pixels.

9. A method according to claim 1, wherein after said identifying of the collagen areas in the second image and before operation (1c), the method further comprises: identifying boundary pixels of lumens in the first image;
locating boundary pixels of lumens in the second image using the identified boundary pixels of lumens in the first image; locating image pixels in the second image which belong to the identified collagen areas and which are neighbouring the located boundary pixels of lumens in the second image;
and dividing the identified collagen areas by classifying said located image pixels in the second image as belonging to the collagen areas not indicative of fibrosis and any remaining pixels in the identified collagen areas as belonging to the collagen areas indicative of fibrosis, such that the identified collagen areas are divided into collagen areas indicative of fibrosis and collagen areas not indicative of fibrosis.

10. A method according to claim 9, wherein said identifying of boundary pixels of lumens in the first image comprises:
identifying a group of image pixels representing lumens in the first image;
forming an initial mask from the first image by setting the group of image pixels representing lumens in the first image as foreground pixels and remaining pixels in the first image as background pixels;
forming a new mask by converting foreground pixels in the initial mask corresponding to image pixels along object boundaries in the first image to background pixels; and
subtracting the new mask pixel-by-pixel from the initial mask to form a difference mask indicating locations of the boundary pixels of lumens in the first image.

11. A method according to claim 10, wherein after said forming of the initial mask and before said forming of the new mask, the method further comprises filling holes in areas formed by the foreground pixels in the initial mask.

12. A method according to claim 9, wherein said locating of image pixels in the second image which belong to the identified collagen areas and which are neighbouring the located boundary pixels of lumens is performed using a region growing method with the located boundary pixels of lumens as starting pixels, wherein the region growing method comprises iteratively locating image pixels in the second image until a number of most recently located image pixels is less than a number of image pixels located in a first iteration.

13. A method according to claim 1, wherein operation (1b) further comprises:
identifying lumens in the first image;
locating groups of clustered lumens from the identified lumens;
determining if each of the identified lumens belongs to a group of clustered lumens; and
identifying each group of clustered lumens as a portal tract and each lumen not belonging to any group of clustered lumens as a central vein.

14. A method according to claim 13, wherein after said identifying of lumens in the first image and before said locating of groups of clustered lumens from the identified lumens, the method further comprises excluding lumens with irregular shapes from the identified lumens.

15. A method according to claim 13, wherein said locating of groups of clustered lumens from the identified lumens comprises:
generating a set of lines connecting each identified lumen to its natural neighbouring identified lumens;
extracting spatial texture features of each identified lumen based on the generated set of lines connected to the each identified lumen; and
clustering the identified lumens based on the extracted spatial texture features to thereby perform said locating of the groups of clustered lumens from the identified lumens.

16. A method according to claim 15, further comprising identifying portal tract regions and central vein regions based on the following:
- forming a plurality of polygons by generating a polygon for each identified lumen, the polygon enclosing intermediate identified lumens closer to the identified lumen than to other identified lumens; and
- for each polygon, identifying a region in the polygon as a portal tract region if the polygon is generated for an identified lumen belonging to a group of clustered lumens and as a central vein region if the polygon is generated for an identified lumen not belonging to any group of clustered lumens.

17. A method according to claim 1, wherein the stage of liver fibrosis is determined using supervised machine learning algorithms or unsupervised clustering algorithms.

18. A method according to claim 1, wherein the first and second images of the input image data relating to the liver comprise three-dimensional image data.

19. A method according to claim 1, wherein the first and second images of the input image data relating to the liver are acquired without staining the liver.

20. A method according to claim 1, further comprising capturing the first and second images of the input image data relating to the liver using a second harmonic generation based imaging system.

21. A computer system having a data storage device and a processor,
- the data storage device storing instructions operable by the processor to cause the processor to determine a stage of fibrosis in a liver based on input image data relating to the liver, the input image data comprising a first image in a Two-Photon Excitation Fluorescence (TPEF) channel and a second image in a Second Harmonic Generation (SHG) channel, wherein the first and second images relate to a tissue structure in the liver and information relating to collagen content in the liver, the processor determining the stage of fibrosis by:
  - identifying a plurality of morphological features of the liver from the first and second images of the input image data relating to the liver, said morphological features comprising collagen areas, said identifying comprising:
    - segmenting a plurality of image pixels in the first image into different groups of image pixels based on intensities of the plurality of image pixels;
    - forming a mask by assigning a weight to each group of image pixels in the first image based on a probability of collagen aggregation in areas comprising the each group of image pixels, wherein each mask pixel comprises one of the assigned weights;
    - applying the mask to the second image to form an enhanced second image with enhanced collagen areas; and
    - segmenting the enhanced second image with the enhanced collagen areas to identify the collagen areas in the second image and to thereby perform said identifying of the plurality of morphological features comprising the identified collagen areas;
  - generating a plurality of measurements based on the identified plurality of morphological features; and
  - automatically determining the stage of fibrosis in the liver based on the generated plurality of measurements.

22. A non-transitory computer program product storing instructions operable by a processor of a computer system to cause the processor to determine a stage of fibrosis in a liver based on input image data relating to the liver, the input image data comprising a first image in a Two-Photon Excitation Fluorescence (TPEF) channel and a second image in a Second Harmonic Generation (SHG) channel, wherein the first and second images relate to a tissue structure in the liver and information relating to collagen content in the liver,
- the instructions being operable to cause the processor to determine the stage of fibrosis by:
  - identifying a plurality of morphological features of the liver from the first and second images of the input image data relating to the liver, said morphological features comprising collagen areas, said identifying comprising:
    - segmenting a plurality of image pixels in the first image into different groups of image pixels based on intensities of the plurality of image pixels;
    - forming a mask by assigning a weight to each group of image pixels in the first image based on a probability of collagen aggregation in areas comprising the each group of image pixels, wherein each mask pixel comprises one of the assigned weights;
    - applying the mask to the second image to form an enhanced second image with enhanced collagen areas; and
    - segmenting the enhanced second image with the enhanced collagen areas to identify the collagen areas in the second image and to thereby perform said identifying of the plurality of morphological features comprising the identified collagen areas;
  - generating a plurality of measurements based on the identified plurality of morphological features; and
  - automatically determining the stage of fibrosis in the liver based on the generated plurality of measurements.

* * * * *